US00PP23631P2

(12) United States Plant Patent
Bliss et al.

(10) Patent No.: US PP23,631 P2
(45) Date of Patent: May 28, 2013

(54) PEACH ROOTSTOCK 'HBOK 27'

(50) Latin Name: ***Prunus persica* L.**
Varietal Denomination: HBOK 27

(75) Inventors: Fredrick A. Bliss, Davis, CA (US); Ali A. Almehdi, Davis, CA (US); Theodore M. DeJong, Davis, CA (US); Craig A. Ledbetter, Clovis, CA (US)

(73) Assignees: The Regents of the University of California, Oakland, CA (US); The United States of America, As Represented By The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/374,776

(22) Filed: Jan. 11, 2012

(51) Int. Cl.
*A01H 5/00* (2006.01)

(52) U.S. Cl.
USPC ..... Plt./183

(58) Field of Classification Search ..... Plt./183
See application file for complete search history.

(56) References Cited

PUBLICATIONS

The Jan. 1, 2008 Test Agreement For Trees/Rootstocks between Fowler Nurseries, Inc. and The Regents of The University of California, 8 pages (redacted).
The Apr. 1, 2008 Test Agreement For Trees/Rootstocks between Washington State University and The Regents of the University of California, 7 pages (redacted).
The Jan. 1, 2010 Test Agreement For Trees/Rootstocks between The Burchell Nursery, Inc. and The Regents of The University of California, 7 pages.
The Jan. 1, 2010 Test Agreement For Trees/Rootstocks between Duarte Nursery, Inc. and The Regents of The University of California, 7 pages.
The Jan. 1, 2010 Test Agreement For Trees/Rootstocks between Fowler Nurseries, Inc. and The Regents of The University of California, 7 pages.
The Jan. 1, 2008 Test Agreement For Rootstocks between Family Tree Farms and The Regents of The University of California, 7 pages.
The Jan. 1, 2010 Test Agreement For Rootstocks between Agronomic National Institute of Tunisia and The Regents of The University of California, 8 pages (redacted).
The Jan. 1, 2011 Test Agreement For Rootstocks between Family Tree Farms and The Regents of The University of California, 6 pages.
The Jan. 1, 2012 Test Agreement For Rootstocks between Wawona Packing Co. LLC and The Regents of The University of California, 7 pages.

*Primary Examiner* — Annette Para
(74) *Attorney, Agent, or Firm* — Morrison & Foerster LLP

(57) ABSTRACT

The new 'HBOK 27' rootstock is an 'OP-F2' plant from an F1 plant of an intraspecific hybrid between two peach parents that is useful as a commercial under-stock for peach and nectarine cultivars. The 'HBOK 27' rootstock has been successfully propagated clonally by leafy cuttings and tissue culture. The 'HBOK 27' rootstock is graft compatible with peach scion cultivars, and confers moderate vigor control to the compound trees. Peach trees grown on the 'HBOK 27' rootstock are productive, require less pruning than trees on grown on the standard rootstock 'Nemaguard', and produce fewer root suckers than 'Nemaguard'. The 'HBOK 27' rootstock shows moderate resistance to root knot nematode [*Meloidogyne incognita* (race 1) isolate 'Beltran'] that is slightly less than that of the standard rootstock 'Nemaguard'.

7 Drawing Sheets

STATEMENT REGARDING FEDERALLY SPONSORED RESEARCH OR DEVELOPMENT

This invention was made with Government support under Grant No. USDA NRICGP 95-37300-1585, awarded by the United States Department of Agriculture National Initiative for Competitive Grants Program, Project 5967-CG. The Government has certain rights in this invention.

Latin name: Botanical/commercial classification: *Prunus persica* L. Batsch new clonal peach rootstock.

Varietal denomination: The varietal denomination of the claimed peach rootstock is 'HBOK 27'.

BACKGROUND OF THE INVENTION

The present invention relates to a new and distinct cultivar of peach rootstock (*Prunus persica*) that has been denominated as 'HBOK 27', and more particularly to a peach rootstock that is graft compatible with peach and nectarine scion cultivars, confers moderate vigor control on compound trees

[approximately 30-40% reduction based on trunk cross sectional area (TCA) and tree height], produces fewer root suckers than the standard rootstock 'Nemaguard', and has moderate resistance to the root knot nematode *Meloidogyne incognita* (race 1) isolate 'Beltran'. Moreover, peach trees grown on the 'HBOK 27' rootstock are productive and require less pruning than trees grown on the standard rootstock 'Nemaguard'.

It is recognized that vigor control of compound trees on a standard rootstock, such as 'Nemaguard', is difficult to achieve and to do so requires extensive pruning both in mid summer and the dormant season. It is also recognized that root suckers produced on standard rootstock are required to be removed manually resulting in costs to the grower. The 'HBOK 27' peach rootstock has moderate vigor control that produces smaller trees, requires less pruning, and produces much fewer root suckers than the standard rootstock 'Nemaguard'. These characteristics result in cost savings for the grower.

The research during which the original tree was first selected as a potential clonal rootstock was conducted at Davis, Calif. In Year 1, the hybrid 'P248-139' was created by crossing 'Harrow Blood' (HB) with 'Okinawa' (OK) at Fresno Calif. 'Harrow Blood' was used as the female parent and 'Okinawa' was used as the male parent in the cross. Seeds resulting from the open pollination of a single $F_1$ plant from hybrid 'P248-139' were used to generate an experimental population (referred to as 'OP-$F_2$ population') in February of Year 5. Fifty seven 'OP-$F_2$' seedlings were budded with 'O'Henry' (referred to as 'O'Henry population') and concurrently each of these seedlings was budded onto 'Nemared' rootstock (referred to as 'OP-$F_2$ population'). Of the 57 budded 'OP-$F_2$' seedlings, 49 were successful bud unions for the seedlings as both a scion and rootstock. However, for seven of the pairs, either the scion union or rootstock union was unsuccessful and had to be re-budded.

The seedling '94-94-27' ('HBOK 27') was one of the bud unions that was re-budded in September of Year 7. After the re-budding, there were no obvious defects in the bud unions, indicating the compatibility of scions and rootstocks. Compound trees of 'O'Henry' scion budded onto each seedling of the 'OP-F2' segregating population as a rootstock were evaluated for trunk cross-sectional area (TCA), tree height, crop yield, cropping efficiency, fruit weight, and number of suckers. Plants of the '94-94-27' seedling were selected for further study of rootstock potential based on field observations of compound plants grown at Davis, Calif. in Year 11 and Year 12. The primary criteria used for choosing seedlings having potential for size control as a rootstock were tree size and TCA. However, other growth and fruit characteristics were also noted. Leafy cuttings collected from the original trees were propagated asexually (rooted), budded with 'O'Henry' peach scion and planted in a replicated field trial under semi-commercial conditions at Parlier, Calif. in Year 15. As a result of that trial 'HBOK 27' was identified as having commercial rootstock potential.

In a separate set of experiments, 7 year-old compound trees of 'HBOK 27', 'HBOK 10', 'HBOK 32', 'HBOK 50', and 'Nemaguard' were studied to determine the mechanism of size control (Tombesi et al., 2011). Compared to those rootstocks and the standard, 'Nemaguard', the new peach rootstock 'HBOK 27' was the most size controlling. Root knot nematode resistance response of each 'OP-F2' seedling in the segregating population was determined using a greenhouse pot test for resistance to *M. incognita*. The test was completed in Year 13, and it was determined that 'HBOK 27' had a moderate resistance rating that was slightly less than the resistant check rootstock 'Nemaguard'.

The new 'HBOK 27' peach rootstock of the present invention has been asexually reproduced by leaf cuttings at Davis, Calif. The distinctive characteristics of the new peach rootstock have been found to be stable and are transmitted to the new rootstocks when asexually propagated.

SUMMARY OF THE INVENTION

The 'HBOK 27' peach rootstock of the present invention is an 'OP-F2' plant from an F1 plant of an intraspecific hybrid between two peach parents that has size control ability, moderate root knot nematode resistance, less wood from dormant and summer pruning, and produces fewer root suckers. When used as a clonally-produced rootstock with fresh market peach ('O'Henry') scions, 'HBOK 27' showed size reduction of compound trees and no evidence of graft incompatibility or other abnormalities. Five year-old compound trees with 'HBOK 27' rootstock had 45% smaller trunk cross-sectional area (TCA) than with the standard rootstock 'Nemaguard'. The compound trees with 'HBOK 27' rootstock also had approximately 50% to 60% less wood from summer and winter pruning, and had fewer root suckers than 'Nemaguard'. Although crop yield per tree usually was less than on 'Nemaguard' rootstock, the compound trees with 'HBOK 27' rootstock that were smaller generally showed greater cropping efficiency. The ability to plant smaller trees at greater density in commercial fields provides an opportunity to recover economically viable yields per unit area. Fruit from the compound trees with 'HBOK 27' rootstock ripened 4 to 7 days later that 'Nemaguard'. The 'HBOK 27' rootstock displays root knot nematode resistance levels that are slightly less than that of 'Nemaguard'. The 'HBOK 27' rootstock is adapted to regions such as California, and can be used as a rootstock for dessert peach, canning peach, almond, apricot, and Japanese plum (*Prunus salicina* Lindl.). Compound plants with 'HBOK 27' rootstocks provide an opportunity for growers to develop new management practices that utilize the potential of these rootstocks to lower costs through size reduction, reduced pruning and less need for sucker control.

DETAILED DESCRIPTION OF THE INVENTION

Figure 1:
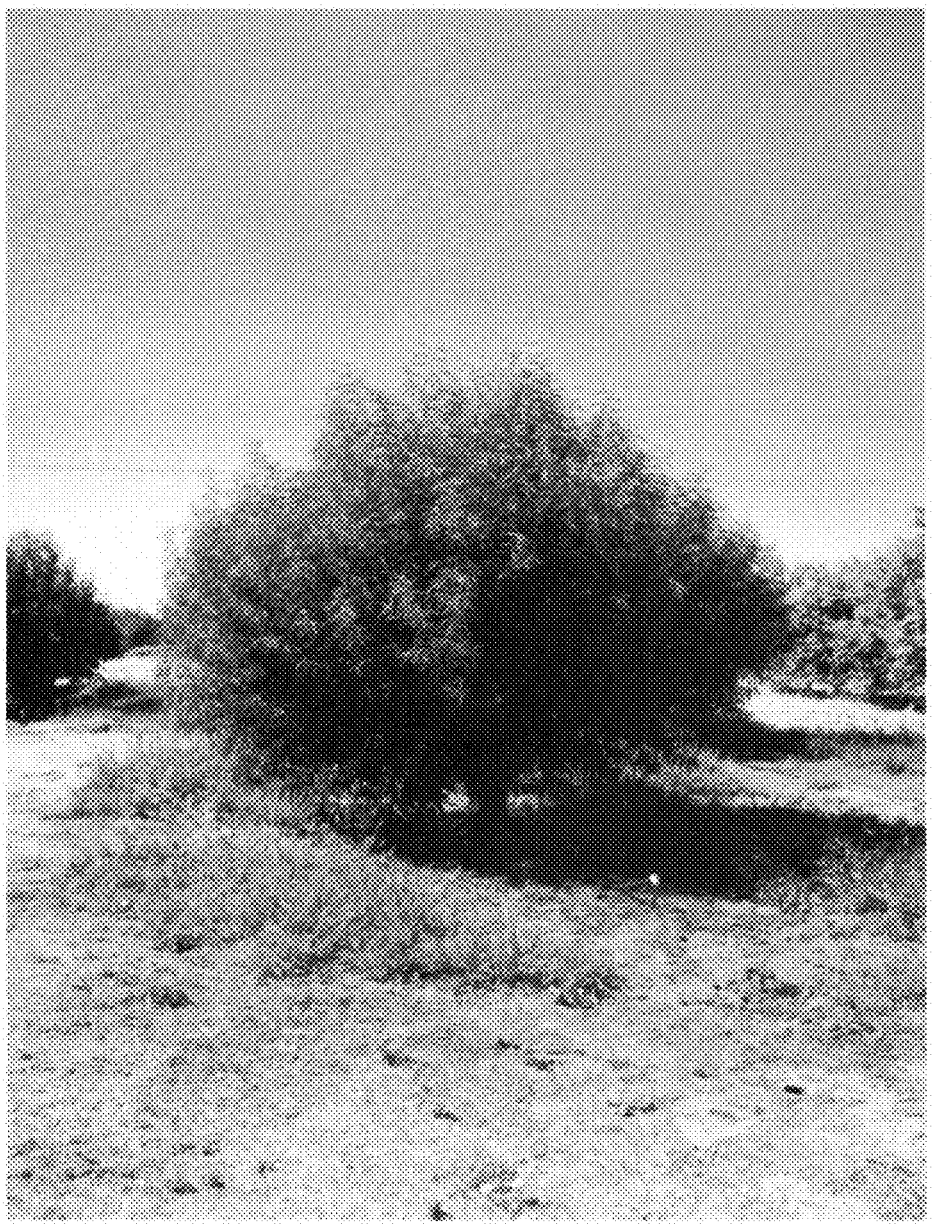
FIG. 1 shows severely cut back tree of 'HBOK 27' in order to encourage vegetative growth for the collection of stem cuttings.

The peach rootstock 'HBOK 27' was developed to be improved rootstocks with size control capability and pest resistance. The peach rootstock was developed by: 1) screening *Prunus* populations for compatibility with and growth controlling potential for peach and nectarine along with resistance to nematodes, crown gall, and bacterial canker; 2) hybridizing parental peach rootstocks with these traits and beginning selection in segregating populations for individuals that possess desired trait combinations; 3) identifying and developing uniform populations from selected individual peach rootstocks that are useful as new seedling rootstocks or asexually propagated clonal rootstocks; and 4) assessing the potential of the best materials for commercial peach and nectarine rootstocks.

'Okinawa' peach was identified as a male parent for its resistance to the nematodes *M. incognita* and *M. javanica*. Additionally 'Okinawa' has a low chill requirement resulting in early blooming and presumably early seed germination. 'Okinawa' is not known to be size controlling and it is an open, standard-type tree on its own root. 'Harrow Blood', selected in Canada as a rootstock, was chosen as the female parent because it was reported to have a dwarfing effect on scions in early years of tree growth. 'Harrow Blood' is susceptible to root knot nematode, has a high chill requirement (late bloom), produces fruit with red flesh, and is a small, 'twiggy' tree.

An experimental population (referred to as 'OP-$F_2$ population') derived from open pollination in Year 5, of a single $F_1$ plant (No. P248-139) of the cross 'Harrow Blood' (HB)× 'Okinawa' (OK) was generated and used.

Seedling rootstocks, including 94-94-27 ('HBOK 27'), for which the first 'O'Henry' budding failed were re-budded with 'O'Henry' in the field during the winter of Year 4 to Year 5 (referred to as 'O'Henry population'). After transplanting and re-budding, the main stems of all plants were pruned to approximately 24 inches and primary lateral branches to about 18 inches. Although the two populations, 'OP-$F_2$population' and 'O'Henry population', were handled differently at the outset, trees within each population received uniform treatment to facilitate detection of genetic differences.

Compound trees of 'O'Henry' scion budded onto each seedling of the 'OP-$F_2$' segregating population as a rootstock were evaluated for trunk cross-sectional area (TCA), tree height, crop yield, cropping efficiency, fruit weight, and number of suckers. Plants of the seedling '94-94-27' ('HBOK 27') were identified for further study of rootstock potential based on field observations of compound plants grown at Davis, Calif. in Year 11 and Year 12 (Tables 1 and 2). The criteria used for choosing seedlings having potential for size control as a rootstock were tree size, TCA, and other growth and fruit characteristics. Leafy cuttings collected from the original trees were propagated asexually (rooted), budded with 'O'Henry' peach scion and planted in a replicated field trial under semi-commercial conditions at Parlier, Calif. in Year 15. As a result of that trial 'HBOK 27' was identified as having commercial rootstock potential. In a separate set of experiments, 7 year-old compound trees of 'HBOK 27', 'HBOK 10', 'HBOK 32', 'HBOK 50', and 'Nemaguard' were studied with the intent of understanding the mechanism of size control (Tombesi et al., 2011).

Table 1 show the characteristics of compound tree growth and fruit of 'O'Henry' scions on controls and 'OP-F2' seedlings used as rootstocks in observation field trials grown at Davis, Calif. for Year 11.

TABLE 1

| Seedling and controls | April, Year 11 Root suckers: Number/tree | April, Year 11 Root suckers: % Control | November, Year 11 Tree height: cm | November, Year 11 Tree height: % Control | November, Year 11 TCA: $cm^2$ | November, Year 11 TCA: % Control |
|---|---|---|---|---|---|---|
| 94-94-1 | 6.0 | 480.0 | 290.0 | 93.5 | 54.6 | 68.3 |
| 94-94-2 | 6.0 | 480.0 | 290.0 | 93.5 | 45.8 | 57.3 |
| 94-94-5 | 1.0 | 80.0 | 230.0 | 74.2 | 19.4 | 24.2 |
| 94-94-8 | 6.0 | 480.0 | 260.0 | 83.9 | 19.1 | 23.9 |
| 94-94-9 | 9.0 | 720.0 | 270.0 | 87.1 | 31.8 | 39.8 |
| 94-94-10 | 17.0 | 1360.0 | 270.0 | 87.1 | 21.7 | 27.1 |
| 94-94-18 | 8.0 | 640.0 | 140.0 | 45.2 | 4.2 | 5.3 |
| 94-94-27 | 11.0 | 880.0 | 255.0 | 82.3 | 33.4 | 41.8 |
| 94-94-29 | 11.0 | 880.0 | 260.0 | 83.9 | 32.2 | 40.2 |
| 94-94-32 | 4.0 | 320.0 | 280.0 | 90.3 | 32.2 | 40.2 |
| 94-94-36 | 7.0 | 560.0 | 140.0 | 45.2 | 7.2 | 9.0 |
| 94-94-40 | 8.0 | 640.0 | 265.0 | 85.5 | 36.8 | 46.0 |
| 94-94-42 | 7.0 | 560.0 | 270.0 | 87.1 | 38.5 | 48.1 |
| Controls (Nemared + Lovell) | 1.3 | 100.0 | 310.0 | 100.0 | 80.0 | 100.0 |

TABLE 1-continued

| Seedling and controls | August, Year 11 Crop yield: Kg/tree | August, Year 11 Crop yield: % Control | August, Year 11 Cropping efficiency: Crop yield/TCA | August, Year 11 Cropping efficiency: % Control | August, Year 11 Fruit weight: g/fruit | August, Year 11 Fruit weight: % Control |
|---|---|---|---|---|---|---|
| 94-94-1 | 21.8 | 94.0 | 0.40 | 137.6 | 218.0 | 94.0 |
| 94-94-2 | 21.6 | 93.1 | 0.47 | 162.5 | 216.0 | 93.1 |
| 94-94-5 | 13.3 | 57.3 | 0.69 | 236.8 | 133.0 | 57.3 |
| 94-94-8 | 9.7 | 41.8 | 0.51 | 175.0 | 97.0 | 41.8 |
| 94-94-9 | 9.5 | 40.9 | 0.30 | 102.9 | 95.0 | 40.9 |
| 94-94-10 | 8.8 | 37.9 | 0.41 | 140.1 | 88.0 | 37.9 |
| 94-94-18 | 0.3 | 1.3 | 0.07 | 24.4 | 30.0 | 31.0 |
| 94-94-27 | 7.9 | 34.1 | 0.24 | 81.5 | 79.0 | 34.1 |
| 94-94-29 | 16.7 | 72.0 | 0.52 | 179.1 | 167.0 | 72.0 |
| 94-94-32 | 14.6 | 62.9 | 0.45 | 156.6 | 146.0 | 62.9 |
| 94-94-36 | 1.6 | 6.9 | 0.22 | 76.8 | 160.0 | 69.0 |
| 94-94-40 | 9.9 | 42.7 | 0.27 | 92.8 | 99.0 | 42.7 |
| 94-94-42 | 10.1 | 43.5 | 0.26 | 90.4 | 101.0 | 43.5 |
| Controls (Nemared + Lovell) | 23.2 | 100.0 | 0.29 | 100.0 | 232.0 | 100.0 |

| Seedling and controls | December, Year 11 Dormant pruning: Kg/tree | December, Year 11 Dormant pruning: % Control |
|---|---|---|
| 94-94-1 | 2.7 | 74.8 |
| 94-94-2 | 1.1 | 31.2 |
| 94-94-5 | 0.7 | 18.7 |
| 94-94-8 | 0.6 | 15.6 |
| 94-94-9 | 1.7 | 46.7 |
| 94-94-10 | 0.7 | 19.9 |
| 94-94-18 | 0.0 | 1.2 |
| 94-94-27 | 1.4 | 37.4 |
| 94-94-29 | 1.5 | 40.5 |
| 94-94-32 | 1.7 | 46.7 |
| 94-94-36 | 0.0 | 1.2 |
| 94-94-40 | 1.6 | 43.6 |
| 94-94-42 | 2.6 | 71.7 |
| Controls (Nemared + Lovell) | 3.6 | 100.0 |

Table 2 shows characteristics of compound tree growth and fruit of 'O'Henry' scions on controls and 'OP-F2' seedlings used as rootstocks in observation field trials grown at Davis, Calif. for Year 12.

TABLE 2

| Seedling and controls | April, Year 12 Root suckers: Number/tree | April, Year 12 Root suckers: % Control | November, Year 12 Tree height: cm | November, Year 12 Tree height: % Control | November, Year 12 TCA: $cm^2$ | November, Year 12 TCA: % Control |
|---|---|---|---|---|---|---|
| 94-94-1 | 7.0 | 280.0 | 280.0 | 95.6 | 66.9 | 71.7 |
| 94-94-2 | 2.0 | 80.0 | 270.0 | 92.2 | 45.8 | 49.1 |
| 94-94-5 | 1.0 | 40.0 | 220.0 | 75.1 | 23.0 | 24.6 |
| 94-94-8 | 8.0 | 320.0 | 220.0 | 75.1 | 23.0 | 24.6 |
| 94-94-9 | 7.0 | 280.0 | 230.0 | 78.5 | 38.5 | 41.3 |
| 94-94-10 | 11.0 | 440.0 | 245.0 | 83.6 | 20.4 | 21.8 |
| 94-94-18 | 25.0 | 1000.0 | 140.0 | 47.8 | 6.4 | 6.9 |
| 94-94-27 | 20.0 | 800.0 | 255.0 | 87.0 | 81.5 | 87.3 |
| 94-94-28 | 11.0 | 440.0 | 230.0 | 78.5 | 42.1 | 45.1 |
| 94-94-29 | 18.0 | 720.0 | 225.0 | 76.8 | 36.1 | 38.7 |
| 94-94-32 | 4.0 | 160.0 | 220.0 | 75.1 | 35.1 | 37.6 |
| 94-94-36 | 13.0 | 520.0 | 245.0 | 83.6 | 38.5 | 41.3 |
| 94-94-40 | 9.0 | 360.0 | 140.0 | 47.8 | 11.5 | 12.3 |
| 94-94-42 | 12.0 | 480.0 | 225.0 | 76.8 | 53.8 | 57.7 |

TABLE 2-continued

| | | | | | | |
|---|---|---|---|---|---|---|
| 94-94-53 | 5.0 | 200.0 | 225.0 | 76.8 | 45.8 | 49.1 |
| Controls (Nemared + Lovell) | 2.5 | 100.0 | 292.5 | 100.0 | 93.3 | 100.0 |

| Seedling and controls | August, Year 12 Crop yield Kg/tree | % Control | August, Year 12 Cropping efficiency Crop yield/TCA | % Control | August, Year 12 Fruit number Per tree | % Control |
|---|---|---|---|---|---|---|
| 94-94-1 | 44.3 | 141.7 | 0.66 | 208.3 | 319.0 | 138.1 |
| 94-94-2 | 18.5 | 59.0 | 0.40 | 126.6 | 141.0 | 61.0 |
| 94-94-5 | 12.8 | 41.0 | 0.56 | 175.4 | 123.0 | 53.2 |
| 94-94-8 | 40.5 | 129.5 | 1.76 | 554.0 | 23.0 | 10.0 |
| 94-94-9 | 21.6 | 69.1 | 0.56 | 176.4 | 105.0 | 45.5 |
| 94-94-10 | 10.8 | 34.5 | 0.53 | 166.8 | 80.0 | 34.6 |
| 94-94-18 | 1.0 | 3.2 | 0.16 | 49.4 | 6.0 | 2.6 |
| 94-94-27 | 15.8 | 50.4 | 0.19 | 60.8 | 110.0 | 47.6 |
| 94-94-28 | 11.7 | 37.4 | 0.28 | 87.4 | 81.0 | 35.1 |
| 94-94-29 | 23.0 | 73.4 | 0.64 | 200.0 | 171.0 | 74.0 |
| 94-94-32 | 18.9 | 60.4 | 0.54 | 169.4 | 150.0 | 64.9 |
| 94-94-36 | 10.6 | 33.8 | 0.27 | 86.4 | 74.0 | 32.0 |
| 94-94-40 | 1.1 | 3.6 | 0.10 | 30.9 | 7.0 | 3.0 |
| 94-94-42 | 14.0 | 44.6 | 0.26 | 81.6 | 102.0 | 44.2 |
| 94-94-53 | 9.5 | 30.2 | 0.21 | 64.9 | 80.0 | 34.6 |
| Controls (Nemared + Lovell) | 31.3 | 100.0 | 0.32 | 100.0 | 231.0 | 100.0 |

| Seedling and controls | August, Year 12 Fruit weight g/fruit | % Control | December, Year 12 Dormant pruning Kg/tree | % Control |
|---|---|---|---|---|
| 94-94-1 | 138.9 | 98.0 | 2.0 | 61.4 |
| 94-94-2 | 130.9 | 92.3 | 0.9 | 27.3 |
| 94-94-5 | 104.3 | 73.6 | 0.7 | 20.5 |
| 94-94-8 | 329.3 | 232.3 | 0.8 | 23.9 |
| 94-94-9 | 205.7 | 145.2 | 1.0 | 30.7 |
| 94-94-10 | 135.0 | 95.3 | 0.7 | 20.5 |
| 94-94-18 | 168.8 | 119.1 | 0.1 | 2.0 |
| 94-94-27 | 143.2 | 101.9 | 2.3 | 68.2 |
| 94-94-28 | 144.4 | 94.7 | 1.8 | 54.5 |
| 94-94-29 | 134.2 | 88.9 | 1.1 | 34.1 |
| 94-94-32 | 126.0 | 100.8 | 1.1 | 34.1 |
| 94-94-36 | 142.9 | 113.4 | 1.2 | 37.5 |
| 94-94-40 | 160.7 | 96.5 | 0.1 | 3.4 |
| 94-94-42 | 136.8 | 83.4 | 1.6 | 47.7 |
| 94-94-53 | 118.1 | 95.5 | 2.1 | 64.8 |
| Controls (Nemared + Lovell) | 135.4 | 100.0 | 1.8 | 100.0 |

Results-Root Knot Nematode Reaction of Clonal Propagules in Greenhouse Pot Tests The root knot nematode resistance response of 'HBOK 27' was determined in a pot test in Year 13. Reactions of clonal propagules of '94-94-27' ('HBOK 27') to root knot nematode [*M. incognita* (race 1) isolate 'Beltran'] were recorded in a greenhouse pot test. Leafy cuttings were taken from the mother tree and rooted. Cuttings were grown for ten months in a greenhouse then given a chilling treatment by growing outside for another two months. Each was re-potted in sand while dormant and then grown for another month in a greenhouse before nematode inoculation. A single inoculation with the isolate was made in May of Year 13 following procedures for inoculum preparation and inoculation as described by Gillen (2001). The test was evaluated in August of Year 13 after incubation for about thee months. Entire root systems of each cutting were scored for gall formation and rated according to the following scale: 0=no galls present — resistant; 1=1-5 galls per plant — moderately resistant; 2=6-10 galls per plant — tolerant; 3=11-15 galls per plant — moderately tolerant; 4=16-20 galls per plant — somewhat tolerant; 5=more than 20 galls per plant—susceptible. 'HBOK 27' received a rating of 1.64 compared to the resistant check 'Nemaguard', which had a rating of 0.0, and the susceptible check 'Lovell' which had a rating of 5.0 (Table 3). Therefore, based on this test 'HBOK 27' was described as being moderately resistant to root knot nematode.

Table 3 shows reactions of clonal propagules of rootstocks grown in a greenhouse pot test and inoculated with root knot nematode [*M. incognita* (race 1) isolate 'Beltran'], at Davis, Calif. in Year 13.

TABLE 3

| Entry | No. of plants | Mean Score | S.E.M. | Reaction |
|---|---|---|---|---|
| Inoculated on May 10, 2002; evaluated Aug. 23, 2002 (I.e. 3 months of incubation). | | | | |
| Hiawatha OP | 10 | 2.3 | 0.72 | Tolerant |
| Sapalta OP | 11 | 3.82 | 0.42 | Mod. tolerant |
| Sapalta OP | 7 | 1.86 | 0.70 | Mod. resistant |
| Sapalta OP | 11 | 4.64 | 0.38 | Some. tolerant |
| Sapalta OP | 5 | 0 | 0 | Resistant |
| 94-94-27 | 11 | 1.64 | 0.29 | Mod. resistant |
| Sapalta OP | 10 | 4.29 | 0.38 | Some. tolerant |
| 96-38-6 | 12 | 0 | 0 | Resistant |
| Sapalta OP | 11 | 5 | 0 | Susceptible |
| Sapalta OP | 11 | 5 | 0 | Susceptible |
| Sapalta OP | 12 | 3 | 0.45 | Mod. tolerant |
| Pumiselect | 11 | 0 | 0 | Resistant |
| Sapalta OP | 16 | 4.44 | 0.31 | Some. Tolerant |
| Sapalta OP | 12 | 0 | 0 | Resistant |
| Lovell | 12 | 5 | 0 | Susceptible |
| Nemaguard | 12 | 0 | 0 | Resistant |
| Inoculated on Mar. 8, 2002; evaluated Aug. 20, 2002 (I.e. 5 months of incubation). | | | | |
| 95-153-141 | 12 | 0 | 0 | Resistant |
| 95-153-121 | 12 | 0 | 0 | Resistant |
| 95-153-137 | 12 | 5 | 0 | Susceptible |
| 95-153-138 | 12 | 0 | 0 | Resistant |
| 95-153-123 | 12 | 0 | 0 | Resistant |
| 95-153-144 | 12 | 0 | 0 | Resistant |
| 95-153-122 | 11 | 0 | 0 | Resistant |
| 94-94-36 | 12 | 0 | 0 | Resistant |

Results-Seedling Selection for Size Control Potential

Compound trees of 'O'Henry' scion budded onto each seedling of the 'OP-$F_2$' segregating population as a rootstock were evaluated for trunk cross-sectional area (TCA), tree height, crop yield, cropping efficiency, fruit weight, and number of suckers. Plants of the 'HBOK 27' seedling were selected for further study of rootstock potential based on field observations of compound plants grown at Davis in Year 11 and Year 12 (Tables 1 and 2). The criteria used for choosing seedlings having potential for size control as a rootstock were tree size, TCA and other growth and fruit characteristics. Leafy cuttings from the original trees were propagated asexually (rooted), budded with 'O'Henry' peach scion and planted in a replicated field trial under semi-commercial conditions at Parlier, Calif. in Year 15.

Performance of 'HBOK 27' in Field Trials

'HBOK 27' rootstock was among several studied in field trials. Data for only 'HBOK 27' and the standard rootstock 'Nemaguard' are presented. Data for all entries in the field trials are found in DeJong et al. (2005, 2006, 2007, 2008 and 2010).

Most of the propagation of these experimental materials for the field experiments was by leafy cuttings at Davis, Calif. Rooted materials were then potted and budded, with chosen scion cultivars, in greenhouses. Compound plants were provided during the winter for planting the following spring.

Performance Comparison of 'O'Henry' Peach Scion on 'HBOK 27' and 'Nemaguard' Rootstocks A field rootstock trial was established at Parlier, Calif. in February Year 15 to measure the growth and productivity of compound trees of scion cultivar 'O'Henry' peach bud grafted onto 'HBOK 27' and 'Nemaguard' rootstocks. A total of 20 trees of each rootstock/scion combination were planted and trained to the perpendicular V system. Between-row spacing was the same for all rootstock/scion combinations [5.49 m (18 ft)] and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest. Supplemental nutrients were provided by applying UN 32 through irrigation at a rate of 5 gal per acre per application of 2 to 3 applications per year until the trees were 2 years old. Beginning in year three, 250 lb per acre of ammonium nitrate was applied each fall. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

The mean values for tree height, trunk cross sectional area (TCA), pruning weights, root suckers, crop yield, cropping efficiency, and individual fruit weight are shown in Table 4. Compared to the standard commercial rootstock, 'Nemaguard', compound trees on 'HBOK 27' were smaller, produced less winter and summer pruning wood, and had fewer root suckers. Crop yield per tree was less for trees with 'HBOK 27' than on 'Nemaguard', but cropping efficiency was greater for 'HBOK 27'. 'O'Henry' on 'HBOK 27' ripened 3-7 days later than on 'Nemaguard' and individual fruit weights were comparable for the two rootstocks (Table 5).

Table 4 shows mean values for tree height, trunk cross sectional area (TCA), crop yield, fruit weight, cropping efficiency, winter pruning weight and summer pruning weight of second-leaf through fifth-leaf 'O'Henry' peach scions on 'HBOK 27' and 'Nemaguard' rootstocks, and mean number of root suckers on each of the rootstocks. Trees were planted at Parlier, Calif. in Year 15.

TABLE 4

| | Trait | | | | | |
|---|---|---|---|---|---|---|
| | Tree height (cm) | | | TCA (cm2) | | |
| Rootstock | Mean | S.E.M. | % control | Mean | S.E.M. | % control |
| Year 16 | | | | | | |
| Nemaguard | 351.6 | 4.2 | 100 | 45.5 | 1.7 | 100 |
| HBOK 27 | 279.0 | 8.2 | 79 | 28.6 | 1.9 | 63 |
| Year 17 | | | | | | |
| Nemaguard | 404.3 | 6.1 | 100 | 73.2 | 2.6 | 100 |
| HBOK 27 | 320.9 | 6.3 | 79 | 45.1 | 2.7 | 63 |
| Year 18 | | | | | | |
| Nemaguard | 453.0 | 5.6 | 100 | 88.8 | 3.7 | 100 |
| HBOK 27 | 392.0 | 9.6 | 87 | 59.5 | 2.7 | 60 |
| Year 19 | | | | | | |
| Nemaguard | 462.6 | 6.1 | 100 | 105.2 | 4.9 | 100 |
| HBOK 27 | 370.5 | 6.3 | 82 | 64.1 | 2.7 | 59 |

| | Trait | | | | | |
|---|---|---|---|---|---|---|
| | Winter pruning weight (kg/tree) | | | Summer pruning weight (kg/tree) | | |
| Rootstock | Mean | S.E.M. | % control | Mean | S.E.M. | % control |
| Year 16 | | | | | | |
| Nemaguard | 7.6 | 0.2 | 100 | NDT* | | |
| HBOK 27 | 3.7 | 0.3 | 49 | NDT* | | |
| Year 17 | | | | | | |
| Nemaguard | 8.4 | 0.4 | 100 | 2.6 | 0.0 | 100 |
| HBOK 27 | 3.9 | 0.3 | 48 | 0.9 | 0.1 | 35 |
| Year 18 | | | | | | |
| Nemaguard | 8.2 | 0.2 | 100 | 4.0 | 0.1 | 100 |
| HBOK 27 | 4.1 | 0.2 | 50 | 1.6 | 0.0 | 40 |
| Year 19 | | | | | | |
| Nemaguard | 5.3 | 0.3 | 100 | 0.9 | 0.0 | 100 |
| HBOK 27 | 2.8 | 0.1 | 44 | 0.3 | 0.0 | 33 |

| | Trait | | | | | |
|---|---|---|---|---|---|---|
| | Root suckers (Number/tree) | | | Crop yield (kg/tree) | | |
| Rootstock | Mean | S.E.M. | % control | Mean | S.E.M. | % control |
| Year 16 | | | | | | |
| Nemaguard | 1.6 | 0.2 | 100 | NDT* | | |
| HBOK 27 | 0.4 | 0.4 | 25 | NDT* | | |
| Year 17 | | | | | | |
| Nemaguard | 3.9 | 0.3 | 100 | 17.0 | 0.8 | 100 |
| HBOK 27 | 0.3 | 0.1 | 8 | 13.8 | 1.5 | 81 |
| Year 18 | | | | | | |
| Nemaguard | 3.7 | 0.2 | 100 | 45.8 | 1.9 | 100 |
| HBOK 27 | 0.2 | 0.1 | 5 | 39.2 | 1.1 | 88 |
| Year 19 | | | | | | |
| Nemaguard | 4.2 | 0.3 | 100 | 48.4 | 1.0 | 100 |
| HBOK 27 | 0.2 | 0.0 | 5 | 39.8 | 0.7 | 82 |

TABLE 4-continued

| | Trait | | | | | |
|---|---|---|---|---|---|---|
| | Cropping efficiency (Crop yield/TCA) | | | Fruit weight (g/per fruit) | | |
| Rootstock | Mean | S.E.M. | % control | Mean | S.E.M. | % control |
| Year 16 | | | | | | |
| Nemaguard | NDT* | | | NDT* | | |
| HBOK 27 | NDT* | | | NDT* | | |
| Year 17 | | | | | | |
| Nemaguard | 0.23 | 0.01 | 100 | 226.8 | 3.3 | 100 |
| HBOK 27 | 0.29 | 0.02 | 126 | 250.9 | 3.1 | 111 |
| Year 18 | | | | | | |
| Nemaguard | 0.47 | 0.03 | 100 | 232.0 | 5.4 | 100 |
| HBOK 27 | 0.68 | 0.04 | 145 | 215.0 | 2.5 | 83 |
| Year 19 | | | | | | |
| Nemaguard | 0.50 | 0.0 | 100 | 210.6 | 2.9 | 100 |
| HBOK 27 | 0.70 | 0.0 | 140 | 198.6 | 1.6 | 94 |

NDT* = No Data Taken because trees were too small.

Tables 5A, 5B, and 5C show crop yield and weight of fruit harvested from the scion cultivar 'O'Henry' on 'HBOK 27' and 'Nemaguard' rootstocks grown at Parlier, Calif. in Year 20 and Year 21.

TABLE 5A

| | Crop yield (Kg/tree) | | | | | |
|---|---|---|---|---|---|---|
| | Number | | | % total | Fruit Wt. | |
| | of tress | Mean | S.E.M. | crop yield | Mean | S.E.M |
| Year 20 | 1st pick: July, 30 Year 20 | | | | | |
| HBOK 27 | 3* | 1.8 | 0.1 | 4.2% | 292.3 | 19.9 |
| Nemaguard | 19 | 22.9 | 1.5 | 45.4% | 213.6 | 4.4 |
| Year 21 | 1st pick: August, 13 Year 21 | | | | | |
| HBOK 27 | 0 | 0 | 0 | 0.0% | 0 | N/A |
| Nemaguard | 19 | 26.2 | 1.8 | 49.3% | 217.8 | 7.4 |

| | Crop yield (Kg/tree) | | | | | |
|---|---|---|---|---|---|---|
| | Number | | | % total | Fruit Wt. | |
| | of tress | Mean | S.E.M. | crop yield | Mean | S.E.M |
| Year 20 | $2^{nd}$ pick: August, 3 Year 20 | | | | | |
| HBOK 27 | 20 | 22.3 | 1.7 | 50.8% | 225.0 | 5.3 |
| Nemaguard | 19 | 16.1 | 1.6 | 31.9% | 198.8 | 2.8 |
| Year 21 | $2^{nd}$ pick: August, 17 Year 21 | | | | | |
| HBOK 27 | 20 | 28.0 | 1.2 | 59.1% | 218.2 | 4.2 |
| Nemaguard | 19 | 19.7 | 1.0 | 37.1% | 203.1 | 2.7 |

TABLE 5B

| | Crop yield (Kg/tree) | | | | | |
|---|---|---|---|---|---|---|
| | Number | | | % total | Fruit Wt. | |
| | of tress | Mean | S.E.M. | crop yield | Mean | S.E.M |
| Year 20 | $3^{rd}$ pick: August, 7 Year 20 | | | | | |
| HBOK 27 | 17 | 23.2 | 1.5 | 45.0% | 191.5 | 4.8 |
| Nemaguard | 16 | 13.5 | 1.3 | 22.5% | 170.8 | 4.0 |
| Year 21 | $3^{rd}$ pick: August, 20 Year 21 | | | | | |
| HBOK 27 | 20 | 7.5 | 0.6 | 15.9% | 215.2 | 4.0 |
| Nemaguard | 19 | 7.2 | 0.9 | 13.6% | 163.7 | 5.6 |

TABLE 5B-continued

| | Crop yield (Kg/tree) | | | | | |
|---|---|---|---|---|---|---|
| | Number | | | % total | Fruit Wt. | |
| | of tress | Mean | S.E.M. | crop yield | Mean | S.E.M |
| Year 20 | No $4^{th}$ pick in Year 20 | | | | | |
| HBOK 27 | N/A | N/A | N/A | N/A | N/A | N/A |
| Nemaguard | N/A | N/A | N/A | N/A | N/A | N/A |
| Year 21 | $4^{th}$ pick: August, 24 Year 21 | | | | | |
| HBOK 27 | 20 | 11.8 | 1.4 | 25.0% | 181.9 | 3.8 |
| Nemaguard | 0 | 0 | 0 | 0.0% | 0 | N/A |

TABLE 5C

| | Number | Crop yield (Kg/tree) | | |
|---|---|---|---|---|
| | of tress | Mean | S.E.M. | % total crop yield |
| Year 20 | Total picked in Year 20 | | | |
| HBOK 27 | 20 | 43.9 | 2.0 | 100% |
| Nemaguard | 19 | 50.3 | 2.5 | 100% |
| Year 21 | Total picked in Year 21 | | | |
| HBOK 27 | 20 | 47.5 | 1.3 | 100% |
| Nemaguard | 19 | 53.2 | 1.2 | 100% |

Tombesi et al. (2011) also reported that the TCA of compound trees of 'O'Henry' scions on 'HBOK 27' rootstock were approximately 40% of that of 'O'Henry' on 'Nemaguard' rootstocks and that the winter pruning weight was one-third that of 'O'Henry' on 'Nemaguard'. Tombesi et al. (2011) also found that the vigor-control capacity of the rootstocks 'HBOK 50', 'HBOK 32', 'HBOK 10', and 'HBOK 27' was strongly related to the xylem hydraulic characteristics of each rootstock, with the latter being the least vigorous [see Table 1 in Tombesi et al. (2011)].

Propagation of 'HBOK 27' for Rootstocks

Asexual propagation of peach rootstock planting materials is usually performed by one of three methods: leafy cuttings, hardwood (dormant) cuttings, and tissue culture. Most of the propagation of these experimental materials for the field experiments was by leafy cuttings at Davis, Calif.

Propagation Via Leafy Cuttings

Materials were propagated using leafy cuttings. Stems were collected from June through August. They were cut into segments 6 to 10 inches long and the leaves near the base were stripped away. Cuttings were then dipped in 1000 ppm IBA (dissolved in 50% ethyl alcohol) for five seconds and the base then placed in a soil-less mix of 1 part vermiculite and 2 parts perlite in propagation flats. Flats were placed under mist, with the frequency of misting regulated by an artificial leaf. Rooting occurred in about two to three weeks.

Propagation Via Hardwood (Dormant) Cuttings

Materials were propagated using hardwood cuttings. Current year shoots were collected in the middle of November. Shoots were cut to 14 inch long and the basal ends were soaked for 24 hours in a 100 ppm IBA. They were then placed in moist burlap bags, which were then placed in plastic bags, securely closed with a wire, and incubated at about 60° F. Cuttings were inspected every week starting after the second week of incubation. When the bases of most cuttings were covered with callus, they were planted in paper sleeves with soil-less mix of three parts fir bark and one part sand. They were placed under cover to protect from rain, and watered whenever needed.

Propagation Via Tissue Culture

Materials were propagated using tissue culture. The procedures involved collecting young shoots, usually in April, and then sterilizing them with a surface sterilizing agent such as common household bleach. The shoots were then rinsed several times with sterile water, and cut into small pieces each containing vegetative terminal or auxiliary buds. These cuttings were then placed in special media for tissue establishment. They were transferred into shoot multiplication medium where auxiliary shoots proliferate in numbers dependent on the type of rootstock. These multiplied shoots were cut and placed in a rooting medium to produce complete plants. The plants were taken out from the test tubes, where they were grown in the laboratory, placed in trays with soilless mix, and transferred into a greenhouse with fogging system for hardening. These were individually potted and transferred to a regular greenhouse where they were budded with different *Prunus* tops, grown till winter, and sold to farmers.

BOTANICAL DESCRIPTION OF THE PLANT

This rootstock resulted from a cross of 'Harrow Blood' peach×'Okinawa' peach made in Year 1. A resulting hybrid was used to produce open-pollinated seedlings that were grafted with free stone peach 'O'Henry' scions and planted at Davis, Calif. However, the bud of 'O'Henry' did not take on the 'HBOK 27' seedling. The rootstock was re-budded with 'O'Henry' again in September of Year 7, and the trees were evaluated for Year 11 and Year 12. Evaluation involved size of the trees, rootstock-scion compatibility, and suckering. Reaction to root knot nematode (*Meloidogyne incognita*) was evaluated in Year 13. Individual seedling rootstocks that showed reduction in total size of the compound tree, graft compatibility, absence or low suckering, and moderate resistance to root knot nematode were selected. Rooted cuttings were grafted with the scion 'O'Henry' peach and planted in a replicated trial at Parlier, Calif. in Year 15. The results showed that scions grafted on this rootstock had height, winter and summer pruning, and number of suckers significantly smaller than scions on the standard rootstock 'Nemaguard'. Crop efficiency was also significantly higher than on 'Nemaguard'.

Other attributes of 'HBOK 27' include the ability to be propagated by rooting of stem cuttings; good anchorage; susceptibility to crown gall; and moderate resistance to root knot nematode The following horticultural description was from plant material of 'HBOK 27' rootstock cultivar growing at Davis, Calif. Trees of 'HBOK 27' were observed for botanical description during Year 19 through Year 22 growing seasons. At that time, the trees had been growing from their twelfth to their fourteenth year, respectively. Color definition used throughout the following botanical description of 'HBOK 27' was set by Munsell Color Chart for Plant Tissues standards, expect for flower pedicels, which was set by Nickerson Color Fan standards.

Tree:

*Tree*.—The tree from which this description is taken was grafted on 'Nemared' and planted at Davis, Calif., in Year 7. It was used as a source from which to propagate the new rootstock for experimental tests and plantings. The propagated tree was grown in a V-shaped training system for two years. Since then, the tree has received rather severe annual pruning to keep it in a highly vegetative state. The heavy pruning favors the development of many long straight shoots especially suited for the production of clonal rooted cuttings (FIG. 1). The trees of 'HBOK 27' are vigorous and hardy under typical Sacramento Valley, Calif. climatic conditions.

Figure 2:
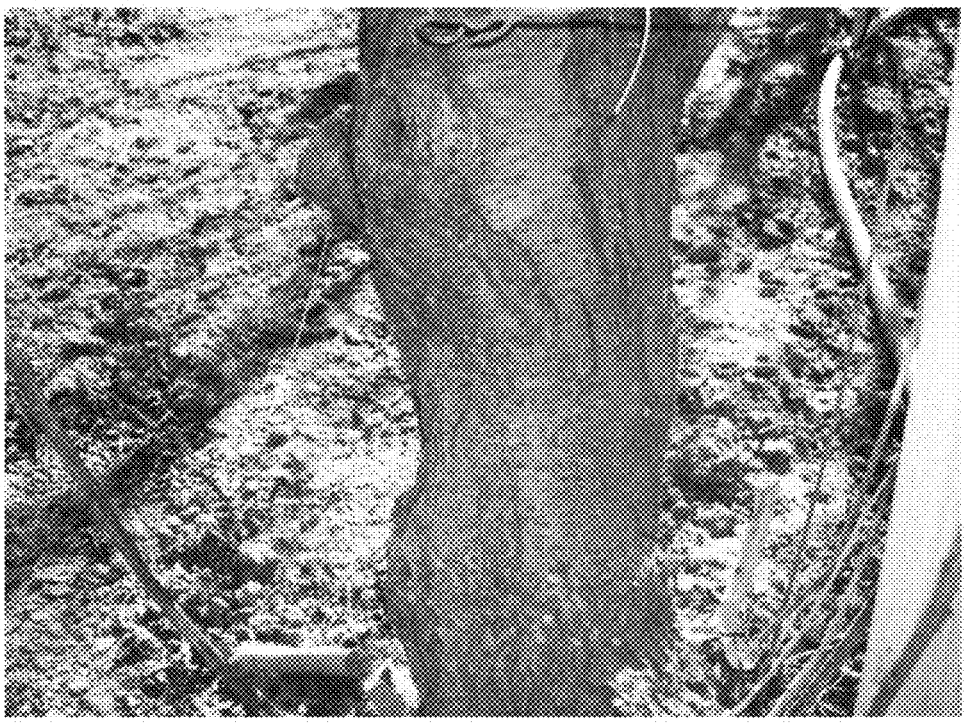
FIG. 2 shows the trunk of 'HBOK 27' grafted on 'Nemared'. The graft union here is undistinguishable.

Trunk:

*Trunk*.—The rootstock was grafted on 'Nemared' and the union between the two rootstocks was so complete that the point of the graft union, after fourteen years, was undistinguishable (FIG. 2). The circumference of the trunk of 'HBOK 27' averages 40 cm when measured 20 cm above the soil level. The trunk surface is coarse and has a moderate number of cracks. Trunk color is yellow red (7.5YR 8/2 by Munsell Color Chart for Plant Tissues standards).

Figure 3:
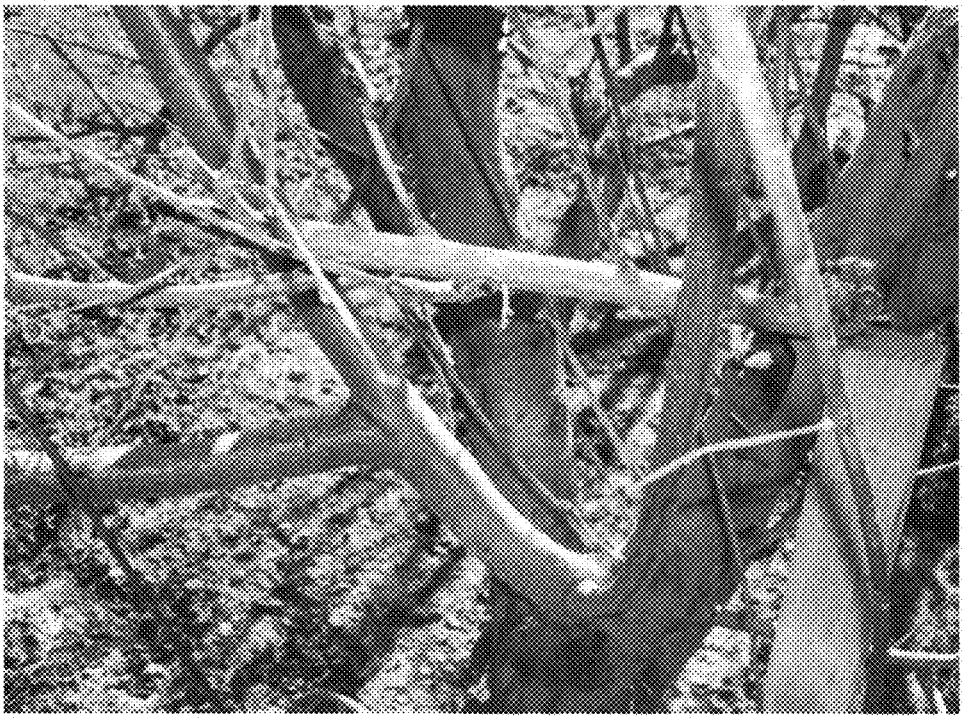
FIG. 3 shows the trunk, scaffolds, and upper spreader branches of 'HBOK 27' grafted on 'Nemared'.
Figure 4:
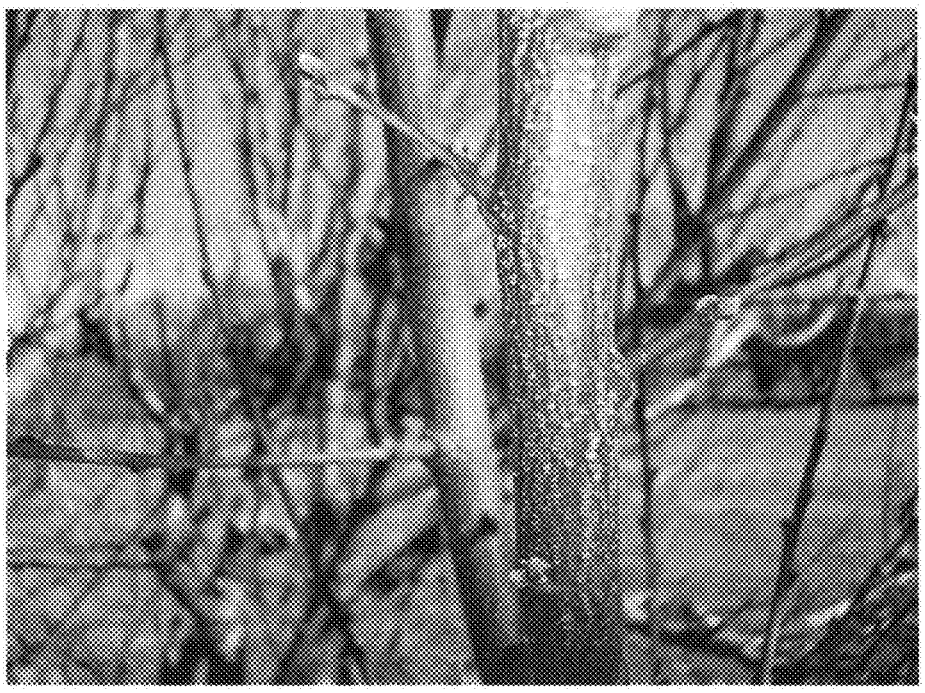
FIG. 4 shows small and flattened bark lenticels from 'HBOK 27' wood. Bark lenticels are present on two to four year old wood of 'HBOK 27'.

Branches:

*Branches*.—The tree branches have the normal thickness of a peach. The primary scaffolds arising from the trunk range from 27 to 29 cm in circumference when measured at the base. Color of the main scaffolds is yellow red (7.5YR 8/2 by Munsell Color Chart for Plant Tissues standards). Base circumference of upper spreader limbs ranges from 10 cm to 12 cm (FIG. 3). Lower and smaller hanger's woods base ranges from 1.5 cm to 2 cm in circumference. Older branch surfaces are netted and lightly furrowed. Surface color of four year old branches ranges from red (2.5R 4-11 to 2.5R5-4 by Munsell Color Chart for Plant Tissues standards). Numerous small and flattened bark lenticels are present on two to four year old wood and absent on one year and older than four year old wood (FIG. 4). Lenticel size ranges from 0.5 mm to 1 mm in width and 2 mm in length. Lenticel color is yellow red (7.5YR 8/2 by Munsell Color Chart for Plant Tissues standards).

Figure 5:
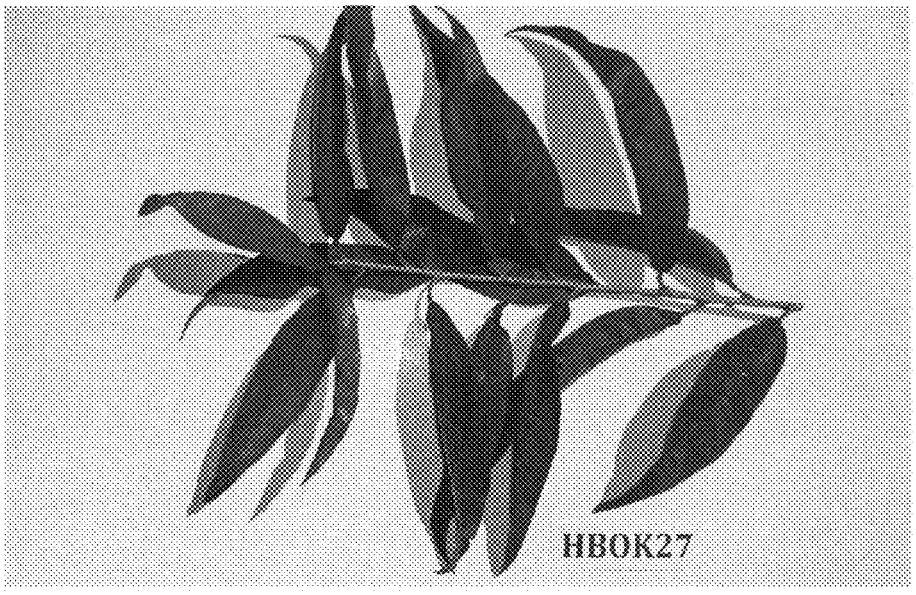
FIG. 5 shows a vegetative branch of 'HBOK 27'.

Leaves:

*Leaves*.—The length of leaves, selected from the middle of shoots bearing fruits, ranges between 10 cm to 13 cm, including the petiole. The width of leaves, measured at the widest point, ranges from 3 cm to 3.2 cm. Leaf shape is subulate; the tip is acuminate; the base is acute; the venation is netted; and the surface is glabrous (FIG. 5). a) Leaf margins Leaf margin is serrulate and at the tip of each of the indentation there is a protrusion that resembles a small spine with a red color (2.5R-4/8 set by Munsell Color Chart for Plant Tissues standards). b) Leaf Color The color of the upper surface of the leaf in mid July, is green yellow (5GY 4-4 set by Munsell Color Chart for Plant Tissues standards). c) Leaf Petiole The petiole is of the average size. The color is green yellow (5GY 6-4 set by Munsell Color Chart for Plant Tissues standards). The length ranges from 5 mm to 10 mm and the thickness is 1 mm. They are glabrous. The stipules are absent. d) Leaf Glands All leaf glands are reniform in shape and located on the petiole portion closest to the leaf blade. Leaf glands range in number from 1 to 2 per leaf. The color of the glands is red (2.5 R 5/4 set by Munsell Color Chart for Plant Tissues standards).

Figure 6:
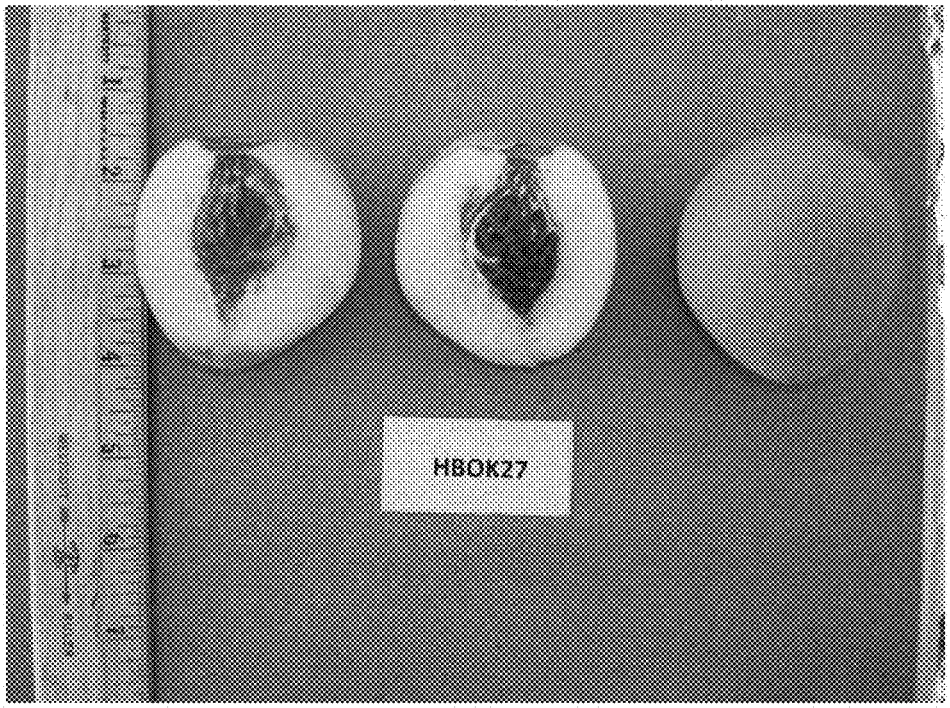
FIG. 6 shows fruits of 'HBOK 27'.

Fruit:

*Fruit*.—The fruit is free stone. The fruit ripens in the middle to the third week of August in Davis, Calif. Fruit surface, resembling an average peach, is pubescent. Fruit shape is round with length equal to the width ranging from 50 mm to 60 mm in diameter (FIG. 6). The tree produces an abundance of fruits and may break branches if not thinned. The average weight of the mature fruit is 77.7 grams. a) Fruit Color The color of fruit skin is green yellow (2.5 GY 8-12 set by Munsell Color Chart for Plant Tissues standards) — (FIG. 6). b) Fruit Flesh Generically, 'HBOK 27' produces white-fleshed peach fruit. The specific color of the fruit flesh when the fruit is between mature and ripe is yellow green (22-1 set by Munsell Color Chart for Plant Tissues standards). The color of the flesh adjacent to the seed is reddish (7.5YR-7/6 set by Munsell Color Chart for Plant Tissues standards) — (FIG. 6).

Seed:

*Seed*.—The seed (pit), resembling a typical peach seed, is ovate in shape with protrusion at the tip and deep grooves on the surface. The average length, including the protrusion, is 30 mm and the average width is 22 mm. Seed color is yellow red (7.5 YR 4-4 set by Munsell Color Chart for Plant Tissues standards) — (FIG. 6). a) Seed Kernel The kernel of the seed is ovate in shape with an average length of 1.7 mm and an average width of 1.2 mm. The color of the kernel is yellow red (5 YR 6/8) with red (2.5 YR 5/6) lines running lengthwise. The seed kernel of 'HBOK 27' resembles a typical peach seed kernel and is bitter in taste.

Figure 7:
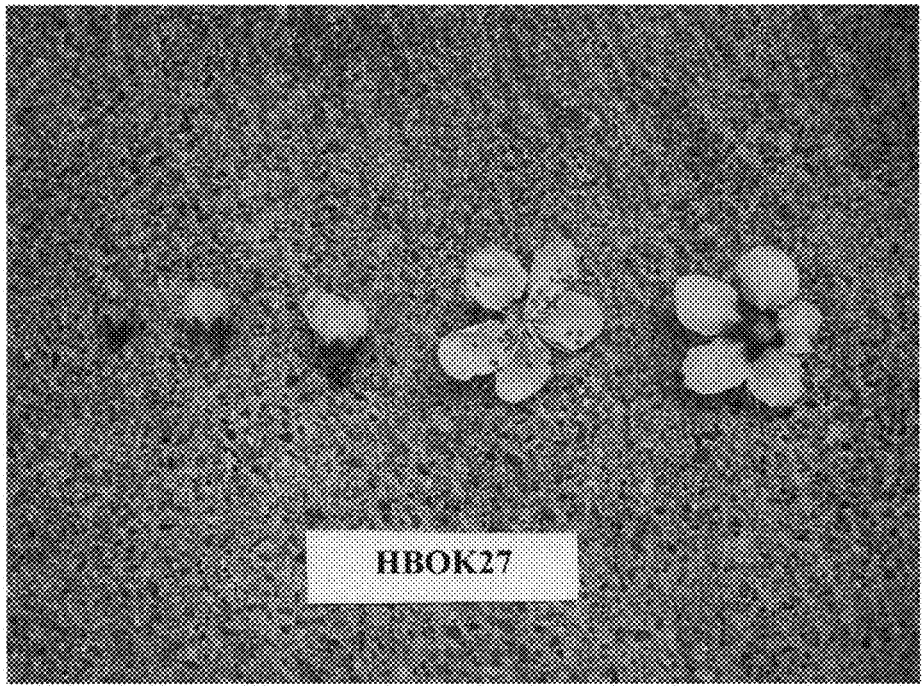
FIG. 7 shows flowers and flower buds of 'HBOK 27' at different stages.

Floral description:

*a*) *Flower buds*.—I. Size The flower buds are medium in size, with an average length of 5 mm and an average width of 3.5 mm when first swelling (FIG. 7). II. Arrangement One flower bud is usually born on each side of a vegetative bud. One vegetative bud is born on each node of one-year old wood. III. Form The flower buds are conic in form and relatively plump. The buds are hardy under typical Sacramento Valley climatic conditions. IV. Color Sepals are red (2.5R-4-4 set by Munsell Color Chart for Plant Tissues standards) — (FIG. 7). V. Bud Surfaces The surfaces of the sepals are heavily pubescent on the margins and gradually less pubescence is evident towards the center of the sepals.

*b*) *Bloom timing*.—The time of bloom is early in relation to standard commercial peach cultivars grown in the Sacramento Valley climatic conditions. Average date of first bloom is February 27. Average date of full bloom is March 6th. The start of leafing coincides with full bloom.

*c*) *Flower size*.—Average flower diameter, in a fully expanded condition, is 40 mm (FIG. 7).

*d*) *Bloom quantity*.—Bloom quantity is heavy when compared with standard commercial peach cultivars grown in the Sacramento Valley climatic conditions. The number of flower buds per node ranges from 1 to 3 with an average of two being most common. Many of the flower buds are retained on the tree to full bloom.

*e*) *Flower petals*.—The number of the petals per flower is five. The average length of the flower petal is 20 mm and the average width is 15-17 mm, in a fully expanded flower (FIG. 7). The shape of the petals is orbicular with margins that are entire. Each of the petals has nine main ribs palmate with net arranged veins. The color of the petals color is pink (2.5R-9/3 set by Munsell Color Chart for Plant Tissues standards) and gets a little more intense in color towards the base (2.5R-8/5 set by Munsell Color Chart for Plant Tissues standards).

*f*) *Flower pedicels*.—The average length and the width of each of the flower pedicels in a fully expanded flower is 1 mm. The color of the pedicel is green yellow (2.5GY-7/8 set by Nickerson Color Fan standards) — (FIG. 7). The surface of the pedicel is glabrous.

*g*) *Sepals*.—The number of the sepals is five. The surfaces of the sepals are heavily pubescent on the margins and gradually less in pubescence towards the center. The form is conic with a round apex. The average width of the upper part, measured at the middle point, is 4 mm; and the average width of the lower part is 2 mm. The color of the sepals, in a fully expanded flower, is red (2.5R-4/6 set by Munsell Color Chart for Plant Tissues standards) — (FIG. 7). The lower section of the sepals, from the early stages of the popcorn state to fully expanded flowers, has red dots. The color of the dots is the same as the sepals at the fully expanded state of the flower.

*h*) *Anthers and pollen*.—The number of anthers averages between 38 and 46. The size of the anthers is average. During the popcorn stage of flower bud development, the color is red (5R-5/10 set by Munsell Color Chart for Plant Tissues standards) dorsally and around the edges ventrally (FIG. 7). Pollen is medium in availability. Pollen color is yellow (2.5Y-8/12 set by Munsell Color Chart for Plant Tissues standards).

*i*) *Stamens*.—The average number of stamens is 40. Stamen length ranges from 11 mm to 19 mm in a fully expanded flower. Color of stamen is red (2.5R-8/4 set by Munsell Color Chart for Plant Tissues standards) — (FIG. 7).

*j*) *Pistil*.—The pistil length ranges from 18 mm to 20 mm. The pubescent ovary has an average length of 2 mm and an average width of 1 mm. The style has an average length of 18 mm and an average width of 0.3 mm. The stigma has an average length of 0.5 mm and an average width of 0.2 mm. The color of the style is yellow (7.5Y-9/8 — set by Munsell Color Chart for Plant Tissues standards). The color of the ovary, after removing the hairs is green yellow (2.5GY-6/8 set by Munsell Color Chart for Plant Tissues standards).

The following references are incorporated by reference for the purpose of providing further comparative data related to the claimed plant material.

DeJong, T., A. Almehdi, S. Johnson and K. Day. 2005. Improved rootstocks for peach and Nectarine. California Tree Fruit Agreement, Annual Report-2005. 20 pp.

DeJong, T., A. Almehdi, S. Johnson and K. Day. 2006. Improved rootstocks for peach and Nectarine. California Tree Fruit Agreement, Annual Report-2006. 18 pp.

DeJong, T., A. Almehdi, S. Johnson and K. Day. 2007. Improved rootstocks for peach and Nectarine. California Tree Fruit Agreement, Annual Report-2007. 19 pp.

DeJong, T., A. Almehdi, S. Johnson and K. Day. 2008. Improved rootstocks for peach and Nectarine. California Tree Fruit Agreement, Annual Report-2008. 19 pp.

DeJong, T., L. Grace, S. Castro, S. Johnson and K. Day. 2010. Improved rootstocks for peach and nectarine. California Tree Fruit Agreement, Annual Report-2010. 25 pp.

Dirlewanger, E., E. Graziano, T. Joobeur, F. Garriga-Caldere, P. Cosson, W. Howard and P. Arús. 2004. Comparative mapping and marker assisted selection in Rosaceae fruit crops. Proc. Natl. Acad. Sci. USA 101:9891-9896.

Foolad, M. R., S. Arulsekar, V. Becerra, F. A. Bliss. 1995. A genetic map of *Prunus* based on an interspecific cross between peach and almond. Theor. Appl. Genet. 91:262-269.

Gillen, Anne M. 2001. Developing a Size-controlling and Root-knot Nematode Resistant Peach [*Prunus persica* (L.) Batsch] Rootstock. Ph.D. Dissertation, University of California, Davis. 237 pp.

Howad, W., T. Yamamoto, E. Dirlewanger, R. Testolin, P. Cosson, G. Cipriani, A. J. Monforte, L. Georgi, A. G. Abbott. 2005. Mapping with a few plants: using selective mapping for microsatellite saturation of the *Prunus* reference map. Genetics 171:1305-1309.

Ogundiwin, E. A., C. P. Peace, T. M. Gradziel, D. E. Parfitt, F. A. Bliss and C. H. Crisosto. 2009. A fruit quality gene map of *Prunus*. BMC Genomics 10:587.

Tombesi, S., A. Almehdi and T. M. DeJong. 2011. Phenotyping vigour control capacity of new peach rootstocks by xylem vessel analysis. Scientia Hort. 127:353-357.

What we claim is:

1. A new and distinct variety of peach rootstock designated 'HBOK 27' as shown and described herein.

* * * * *